(12) United States Patent
Guogiao et al.

(10) Patent No.: US 7,851,512 B2
(45) Date of Patent: Dec. 14, 2010

(54) COMPOSITION CONTAINING ARTEMISININ FOR TREATMENT OF MALARIA

(76) Inventors: Li Guogiao, Room 601, Building 66, 12 Airport Road, Guangzhou (CN) 510405; Jianping Song, Room 601, Building 66, 12 Airport Road, Guangzhou (CN) 510405

(*) Notice: Subject to any disclaimer, the term of this patent is extended or adjusted under 35 U.S.C. 154(b) by 516 days.

(21) Appl. No.: 10/587,277

(22) PCT Filed: Sep. 20, 2004

(86) PCT No.: PCT/CN2004/001064

§ 371 (c)(1),
(2), (4) Date: Jul. 25, 2006

(87) PCT Pub. No.: WO2005/030197

PCT Pub. Date: Apr. 7, 2005

(65) Prior Publication Data

US 2006/0281785 A1 Dec. 14, 2006

(30) Foreign Application Priority Data

Sep. 26, 2003 (CN) ................................ 03 1 46951

(51) Int. Cl.
*A61K 9/20* (2006.01)
*A61K 31/47* (2006.01)
*A61K 31/335* (2006.01)
*A01N 43/42* (2006.01)
*A01N 43/32* (2006.01)

(52) U.S. Cl. .................. 514/895; 424/464; 514/313; 514/452

(58) Field of Classification Search .................. None
See application file for complete search history.

(56) References Cited

U.S. PATENT DOCUMENTS

| | | | |
|---|---|---|---|
| 5,219,865 A | 6/1993 | Chatterjee et al. | |
| 5,270,037 A | 12/1993 | Bienzle | |
| 7,670,631 B2 | 3/2010 | Mota et al. | |
| 2004/0058981 A1* | 3/2004 | Lai et al. | 514/452 |

FOREIGN PATENT DOCUMENTS

| | | |
|---|---|---|
| CN | 1237416 A | 12/1999 |
| CN | 1305810 A | 8/2001 |
| EP | 0290959 | 11/1988 |
| WO | WO-96/40108 A1 | 12/1996 |
| WO | WO-02/26226 A1 | 4/2002 |

OTHER PUBLICATIONS

Giao et al. [online] retrieved from the internet on Dec. 12, 2008: http://resource.actmalaria.net/v1/index.php?m=resource&db=biblio&entry_id=1276&submit_user=Details&search_term=aminoquinoline&search_title=&search_type=&search_author=&search_country=&search_publisher=&search_language=&search_subject=&search_isbn=&search_pubyear=; Dec. 2002; 2 pages.*

White (Phil Trans R Soc Lond B 1999, 354, 739-749).*

Klayman (Science 1985, 228(4703), 1049-1055).*

Denis, M.B. et al., "Efficacy and Safety of Dihydroartemisinin-Piperaquine (Artekin) in Cambodian Children and Adults with Uncomplicated Falciparum Malaria." *Clin. Inf. Dis.* 35(12), 1469-1476 (2002).

Huang, J.R. et al., "A study of artemether combined with primaquine in the treatment of falciparum malaria." *Database Medline (Online)*, U.S. National Library of Medicine, Bethesda, MD, US, 2001, Database Accession No. NLM12572052 (abstract only).

Chawira, N. et al., "The effect of artemisinin combined with standard antimalarials against chloroquine-sensitive and chloroquine-resistant strains of *Plasmodium falciparum in vitro*." *Journal of Tropical Medicine and Hygiene* 90, 1-8 (1987).

Giao, P.T. et al., "CV8, a new combination of dihydroartemisinin, piperaquien, trimethoprim and primaquine, compared with atovaquone-proguanil against falcipraum malaria in Vietnam." *Tropical Medicine and International Health* 9(1), 109-116 (2004).

"Antimalarial Drug Combination Therapy: Report of a WHO Technical Consultation." World Health Organization, 2001, 1-30.

Jaeger, A. et al., "Clinical features and management of poisoning due to antimalarial drugs." *Med. Toxicol. Adverse Drug Exp*. Jul.-Aug. 1987; 2(4): 242-73.

Srivastava, P. et al., "Glutathione S transferase activity in malarial parasites." *Tropical Medicine and International Health* 4(4), Jan. 5, 2002, 251-254.

Song, J. et al., "Clinical Observation of Dihydroartemisinin and Piperaquine in Treating Falciparum Malaria without Complication." *National Medical Journal of China* 83(12), Jun. 25, 2003, 1099-1100 (original article plus English translation).

* cited by examiner

*Primary Examiner*—Ernst V Arnold
(74) *Attorney, Agent, or Firm*—Connolly Bove Lodge & Hutz LLP

(57) ABSTRACT

The present invention provides a novel combination comprising artemisinin in the form of tablets and related dosage forms for pediatric use, such as granules, suppository, suspension syrup and dry powder, for the treatment of human malarias including multiple-resistant subtertian malaria, tertian malaria and quartan malaria. The combination is comprised of artemisinin, piperaquine and primaquine. Clinical tests in Southeast Asia countries where malaria is epidemic demonstrate that, apart from having high and rapid therapeutic effect possessed by the most excellent domestic and foreign artemisinin-type anti-malarial drugs, the present combination is also featured with shorter course of treatment, less side effect, lower material cost, and more convenience for administration, and its ability of rapidly killing gametophyte and cutting off infection source thereby blocking spreading of malaria is a further improvement.

4 Claims, No Drawings

COMPOSITION CONTAINING ARTEMISININ FOR TREATMENT OF MALARIA

CROSS-REFERENCE TO RELATED APPLICATIONS

The present patent application is a §371 of International Application No. PCT/CN2004/001064 filed on Sep. 20, 2004 and claiming priority to Chinese patent application Ser. No. 03146951.5 filed on Sep. 26, 2003 in the names of Guoqiao Li, et al.

TECHNICAL FIELD

The present invention relates to medicaments for the treatment of malaria, in particular to a combination comprising artemisinin having high and rapid therapeutic effect.

BACKGROUND ART

Among the prior art anti-malaria drugs, some employ artemisinin derivatives (such as dihydroartemisinin, artesunate, artemether, arteether) in conjunction with piperaquine having a long half-life. GI tract side effects such as nausea and vomiting due to substantial amount of phosphates adversely affect the therapeutic effects, with incidence of up to 10% when the total amount for one course is divided into 3 doses, and reduced to 3-5% when divided into 4 doses. In addition, the prior art anti-malaria drugs suffer from the disadvantages of long processing period, high production cost, short shelf life, large dosage and the like.

DISCLOSURE OF THE INVENTION

The object of the present invention is to overcome the shortcomings in the prior art by providing a combination comprising artemisinin, which requires shorter course of treatment, with less side effect, lower production cost, more convenience for administration, as well as high and rapid therapeutic effect.

The object of the present invention is achieved by a combination comprising artemisinin, which can be formulated into tablets and granules, suppository, suspension syrup or dry powder for pediatric use. The combination comprises artemisinin, piperaquine and primaquine in following ratio ranges:

| | |
|---|---|
| artemisinin, | 1 part |
| piperaquine, | 5 parts |
| primaquine, | 0-0.05 part, |
| the optimum ratio being | 1:5:0.04. |

The primaquine can also be formulated into a separate tablet to be taken along with a tablet of mixed artemisinin and piperaquine.

It has been shown through clinical trials of more than 600 cases of multiple-resistant subtertian malaria, tertian malaria and quartan malaria that the present drug is characterized by rapid and high therapeutic effect, low toxicity, short course of treatment, and ability of rapidly eliminating infection source to block spreading of malaria, which is obviously superior to domestic and foreign drugs of the same class in terms of therapeutic effect and function.

EMBODIMENT OF THE INVENTION

The formulation is as follows:

| | |
|---|---|
| Artemisinin | 160 g |
| Piperaquine | 750 g |
| Primaquine | 6 g |
| Adjuvant (hydroxypropyl cellulose and etc.) | q.s. |
| to produce | 1,000 Tablets |

The Preparation Process

Qualified materials are respectively crushed and pass through a screen of 100 meshes. The materials and adjuvant are accurately weighed according to the formulation, and the individual ingredients are homogenously mixed and compressed into tablets or prepared into various dosage forms for pediatric use, which are then packed to give the finished product.

The present combination comprising artemisinin is useful in the treatment of various malarias (human malaria such as subtertian malaria, tertian malaria and quartan malaria), in particular multiple-resistant subtertian malaria. The total dosage for an adult is 2 tablets, with 1 tablet per day.

Primaquine is contained in the present combination in an amount of only 6 mg per tablet, which is the daily dosage and taken for only two days. This dosage is reduced by 82% as compared with a conventional dosage of 67.5 mg in three days. Its use in conjunction with artemisinin, as proved by experiment, can lead to the gametophyte of plasmodium falciparum losing its infectivity completely by 24 h after the first dose, thereby blocking its propagation without any side effect. It is one particular feature possessed by the present combination using an ultra-low dose of primaquine.

Due to its advantages including lower material cost, smaller size, shorter course of treatment, and more convenience for administration (2 tablets in two days for an adult) as well as ability of substantially killing gametophyte to block spreading of malaria, as compared with any artemisinin combinations, the present combination can favorably enter national state hospitals in developing countries at a relatively low price, and is in the interest of global application and dissemination of anti-malaria measures.

The invention claimed is:

1. A composition useful for treatment of malaria in humans resulting in a shorter course of treatment and less side effects consisting of artemisinin, piperaquine and primaquine and adjuvants formulated into tablets or granules, suppositories, suspension syrup or dry powder for pediatric use in following ranges of ratios:
   artemisinin 1 part
   piperaquine 3-9 parts
   primaquine an amount up to 0.2 parts.

2. A composition according to claim 1 wherein primaquine is present at 0.05 parts.

3. A composition according to claim 1 wherein primaquine is formulated into a separate tablet or dose to be taken along with a tablet or dose of mixed artemisinin +piperaquine.

4. A composition according to claim 2 wherein primaquine is formulated into a separate tablet or dose to be taken along with a tablet or dose of mixed artemisinin +piperaquine.

* * * * *